United States Patent [19]

Collins

[11] 4,335,110
[45] Jun. 15, 1982

[54] PHARMACEUTICAL COMPOSITIONS OF SANGUINARIA GALANGAL AND ZINC CHLORIDE

[75] Inventor: Keith R. Collins, Estoril, Portugal
[73] Assignee: Orewa Inc., Estoril, Portugal
[21] Appl. No.: 179,159
[22] Filed: Aug. 18, 1980
[30] Foreign Application Priority Data

Aug. 23, 1979 [GB] United Kingdom ............... 7929364

[51] Int. Cl.³ .................... A01N 59/16; A01N 65/00; A61K 33/30; A61K 35/78
[52] U.S. Cl. .................................... 424/145; 424/49; 424/58; 424/195
[58] Field of Search ................... 424/145, 195, 49, 58

[56] References Cited

U.S. PATENT DOCUMENTS 2,344,830  3/1944  Mohs ................................. 424/145
4,160,821  7/1979  Sipos ................................. 424/145

OTHER PUBLICATIONS

Fitzpatrick; C. A., vol. 48 (1954) 13800a.
Mohs; C. A., vol. 49 (1955) 3370i.
Chopra et al.; C. A., vol. 52 (1958) 13014a.

*Primary Examiner*—Allen J. Robinson
*Attorney, Agent, or Firm*—Sherman & Shalloway

[57] ABSTRACT

A pharmaceutical composition for the treatment of periodontal and other diseases comprises zinc chloride, the active ingredients of sanguinaria and galangal, and purified water as an excipient.

Preferred proportions of the constituents are, by weight: zinc chloride 45%; sanguinaria 10.8%; galangal 7.2%; water 37%. These proportions produce a paste, and an excipient such as petroleum jelly may be added in such a proportion as to produce an ointment. Dilution may be effected by the addition of distilled water or gelatin, and a quantity of the order of 2%, by weight, of sodium carboxy-methyl cellulose may be added as a drying agent.

The pharmaceutical composition may be administered externally, as a paste or ointment, or may be provided in capsules, with gelatin crystals as a buffer, to be taken orally, or may be administered parenterally.

The pharmaceutical composition can be prepared by dissolving zinc chloride in purified water, screening and mixing sanguinaria and galangal and adding the zinc chloride solution to the mixture of sanguinaria and galangal to produce the paste.

11 Claims, No Drawings

PHARMACEUTICAL COMPOSITIONS OF SANGUINARIA GALANGAL AND ZINC CHLORIDE

BACKGROUND OF THE INVENTION

This invention relates to pharmaceutical compositions which are particularly effective in the treatment of periodontal and dental diseases, bilharziasis, and skin infections by pseudomonas aeruginosa, cocci and fungi.

Periodontal disease is a major problem in modern dental practice. In fact, it can be said that practically all dental patients suffer from some type of periodontal disease—and that it is the main cause for the loss of teeth in adults.

The only form of treatment to deal with periodontitis, to date, is surgery and that provides an undesirably high recurrence rate.

SUMMARY OF THE INVENTION

It is the object of the present invention to provide a pharmaceutical composition which is effective in the simple and satisfactory treatment of the above conditions and, according to the invention, the composition essentially comprises the active constituents of sanguinaria and galangal.

Preferably, the composition comprises zinc chloride, sanguinaria, galangal, and purified water as an excipient.

Optimum results have been obtained from a composition having the following constituents, and hereinafter referred to as "Composition KC101":

Zinc chloride: 45%
Deionized or demineralized water: 37%
Sanguinaria (dried rootstock of *Sanguinaria Canadensis*): 10.8%
Galangal (dried rootstock of *Alpina Officinarium*): 7.2%

The invention also provides a method of preparing the pharmaceutical composition, and a method of curative treatment employing the composition.

DESCRIPTION OF THE PREFERRED EMBODIMENT

Method of manufacture of Composition KC101

Utmost care should be exercised in the handling, weighing and mixing of the components. Adequate ventilation and/or dust control (vacuum) may be necessary.

Zinc chloride is dissolved in the deionized water in a Pyrex (heat-resistant glass) container. The solution is filtered through a coarse sintered glass filter, collecting the filtered solution in a Pyrex container. Sanguinaria and galangal which have been passed through a 100 mesh bolting cloth are weighed out. This is done as follows:

(a) an initial weighing of slight excess,
(b) screening to 100 mesh,
(c) reweighing to provide the amount required in the formula.

In operation, an excess is removed from the bulk container adequate to provide sufficient screening material for the product. The whole amount removed from the bulk containers should be recorded on a materials control card.

The excess, after screening, is discarded and not returned to the bulk container.

Mixing: The sanguinaria and the galangal are mixed either in a plastic bag or a stainless steel container. The resulting mixed powder is placed in the pan of a laboratory mixer.

The zinc chloride solution is added to the mixed powder in increments of approximately 300ml. Thorough mixing is carried out following each addition, until the powder has absorbed the liquid. Thorough mixing is, again, carried out when all of the zinc chloride solution has been added to the powder.

Composition KC101 is a dark brown paste with a pleasant odour. This paste remains unaltered without any perserving agents, and needs no refrigeration. Its consistency is not affected by changes either in temperature or in a relative humidity.

Ointments can be prepared using Composition KC101 and Vaseline or any other adequate excipient.

Composition KC101 is disinfectant, antiseptic, caustic and escharotic in its action, depending on its concentration.

It is believed that the effective properties of Composition KC101 are derived primarily from the combined active constituents of zinc chloride, sanguinaria and galangal.

Specific treatments, employing the pharmaceutical composition, will now be described:

1. Treatment of Periodontal Diseases (a) A periodontal disease such as gingivitis or one of the various stages of periodontitis is diagnosed during inspection and thorough cleaning of the mouth and, particularly, the gingiva and teeth.

(b) The area to be treated is dried and isolated, and a layer of not less than 1 mm thick of Composition KC101 is applied to the diseased area, and left in position for at least 10 minutes, after which period the paste is rinsed off and the patient's mouth is cleaned by suction.

(c) This process is repeated, usually one to four times, at periods of 2 to 7 days, at the dental surgeon's discretion, until the disease appears to be clinically cured.

(d) Subsequent visual checks are made to confirm the cure.

As an alternative to the time of treatment-in (b), a dental dressing may be applied over Composition KC101, if a longer period of contact with the paste is felt to be required, for example, in a severe case of periodontitis.

In cases of severe periodontitis with deep pocket formations, another process of application may be used, in which small pieces of sterilized cotton strings are saturated with Composition KC101 and inserted in the periodontal pocket for 10 to 15 minutes. After that period, the piece of cotton string is removed, and the dental surgeon proceeds to the regular rinsing and cleaning of the mouth by suction.

According to the stage of the disease and the individual response, the dental surgeon may use Composition KC101 full strength or diluted—in various percentages—in distilled water or glycerine.

Treatment with Composition KC101 has definite advantages over surgical treatment and, furthermore, the results obtained are equal to and, in most cases, superior to those obtained by surgery. The time for healing after treatment is also considerably shorter than that required by surgery.

2. Treatment of Dental Caries (a) After dental examination and detection of a caries, the carious cavity is thoroughly cleaned and disinfected. Composition KC101 is then applied to the cavity walls. A provisional occulusive dressing is applied over the carious cavity and left for a period of 7 to 15 days.

(b) When the provisional dressing is removed, what remains of Composition KC101—a brown dust—is removed, and, (c) The dental surgeon proceeds to the porcelain filling of the cavity or to the dental restoration with amalgam.

At the dental surgeon's discretion, another treatment may be carried out, before step (c), if the caries is particularly advanced.

The main advantages of this treatment over conventional treatments are:

I: Treatment with Composition KC101 consists of 2 to 4 very short sessions (10 minutes, each, on average) as opposed to several long sessions (40 minutes, each, on average).

II: Drilling is, as a rule, not required.

III: No anesthesia is necessary—this treatment is painless.

IV: No psychological preparation of the patient is needed, as is the case when anesthesia and drilling are to be expected.

V: Treatment is carried out as easily in children as in adults.

VI: Even milk teeth can be submitted to this treatment.

3. Treatment of Bilharziasis (Schistomsomiasis)

This is a very grave infestation, widespread through Asia, Africa and Tropical America.

(a) Capusles are prepared from a mixture of 100 mg of Composition KC101 and gelatin crystals, as a buffer, in gelatin capsules.

(b) A capsule is adminstered to the infected patient morning and night, after meals, each day for about one week to a month. The internal action of the paste kills the eggs of the infesting worms which rapidly die off.

4. Treatment of the *Pseudomonas Aeruginosa*

This usually affects surgical wards in hospitals and, being highly contagious and infectious, spreads rapidly. Current cures may take two weeks or more, and surgical activity must usually be suspended if this infection is present.

(a) An ointment is prepared, comprising between 1% and 5% of Composition KC101 and vaseline (excipient).

(b) A layer of ointment is applied to and around all areas, usually wounds, which are infected by Pseudomonas aeroginosa.

(c) The treated areas are inspected, after about 24 hours and, in almost all cases, the infection should be terminated.

(d) After a further 24 hours, a check is made to ensure that no further, or residual, infections by Pseudomonas aeruginosa exist; the infection can then be regarded as cleared. P Regarding (a), areas where infections by Pseudomonas aeruginosa might be expected may also be treated.

Regarding (c), in the unlikely event of the infection remaining in a treated area, a further layer of more concentrated ointment is applied.

The ointments are used, in a similar manner, also for the treatment of infections by cocci and fungi.

In a development of the invention, initial tests have shown that the effectiveness of the composition may be improved by the incorporation of sodium carboxymethyl cellulose in an amount of the order of 2% by weight. This additive acts as a drying agent for the outer layer, and has effectively stopped "running" after a period of about 1½ hours. The additive, which may be incorporated during manufacture of the composition, has not presented any ecological problems and appears to have no chemical effect on the composition.

Further pharmaceutical uses for the composition according to the invention are being explored and, due to its suggested effectiveness as an anti-bacterial, antifungi, cytotoxic and immunopotentiator, further effective results are expected in the treatment of fungal diseases and microbial diseases, and use in general immunology should be promising.

Furthermore, work is in progress to synthesise the composition, which will, eventually, permit its research in general internal diseases.

Lastly, experiments have already shown that the composition is equally effective in the veterinary field generally, and specifically on horses and cattle.

I claim:

1. A pharmaceutical composition which comprises in approximately the following proportions, by weight: zinc chloride 45%; sanguinaria 10.8%; galangal 7.2%; and water 37%.

2. The composition according to claim 1, and further comprising, as an excipient, petroleum jelly in such a proportion as to produce an ointment-like consistency.

3. The composition according claim 1 or claim 2, and further comprising a quantity of sodium carboxymethyl cellulose effective to thicken said composition.

4. The composition according to claim 3, in which the amount of sodium carboxy-methyl cellulose is approximately 2% by weight of the composition.

5. A pharmaceutical capsule containing a composition according to claim 1 in an amount effective for the treatment of Bilharziasis, and a buffer.

6. The capsule according to claim 5, in which said buffer comprises gelatin crystals.

7. A method of treatment of peridontal or carious disease, comprising administering to the gums or teeth of a patent a pharmacologically effective amount of the composition as claimed in claim 1 and allowing said composition to remain in contact with the gums or teeth for a period of time sufficient to effectively treat said disease.

8. A method of treatment of Bilharziasis comprising administering orally to a patient suffering from Bilharziasis a pharmacologically effective amount of the composition as claimed in claim 1.

9. The capsule according to claim 5 or 6 which comprises about 100 milligrams of said composition.

10. The method of claim 7 wherein said disease is gingivitis and the composition is allowed to remain in contact with the diseased area of the gums for at least ten minutes.

11. The method of claim 7 wherein said disease is dental caries and wherein said composition is applied to the carious cavity and allowed to remain in place for a period of from about 7 to 15 days.

* * * * *